United States Patent [19]

Ward et al.

[11] 4,454,139
[45] Jun. 12, 1984

[54] α2-ADRENOCEPTOR ANTAGONISTIC BENZOQUINOLIZINES

[75] Inventors: Terence J. Ward, Slough; John L. Archibald, Farnham Royal, both of England

[73] Assignee: John Wyeth & Brother, Limited, Maidenhead, England

[21] Appl. No.: 416,399

[22] Filed: Sep. 9, 1982

Related U.S. Application Data

[63] Continuation-in-part of Ser. No. 291,119, Aug. 10, 1981, abandoned.

[30] Foreign Application Priority Data

Aug. 28, 1980 [GB] United Kingdom ................ 8027889
Apr. 16, 1981 [GB] United Kingdom ................ 8112080
Aug. 20, 1981 [GB] United Kingdom ................ 8125468
Oct. 7, 1981 [GB] United Kingdom ................ 8130350

[51] Int. Cl.³ .................... A61K 31/47; C07D 455/06
[52] U.S. Cl. ...................................... 424/258; 546/95
[58] Field of Search .......................... 546/95; 424/258

[56] References Cited

FOREIGN PATENT DOCUMENTS 1513824  6/1978  United Kingdom ................ 546/95

Primary Examiner—Richard A. Schwartz
Attorney, Agent, or Firm—George Tarnowski

[57] ABSTRACT

The invention concerns benzoquinolizines of formula

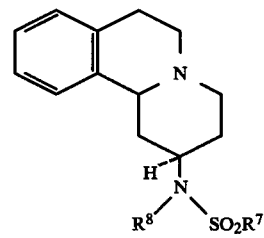

and their acid addition salts. In the formula $R^7$ is lower alkyl or a phenyl or naphthyl radical optionally substituted with specified substituents and $R^8$ is methyl or ethyl. The compounds possess high $\alpha_2$ (presynaptic) adrenoceptor antagonistic activity and a good $\alpha_2/\alpha_1$ antagonistic selectivity.

15 Claims, No Drawings

α2-ADRENOCEPTOR ANTAGONISTIC BENZOQUINOLIZINES

This is a continuation in part of U.S. Ser. No. 291,119, filed Aug. 10, 1981 and now abandoned.

This invention relates to benzoquinolizines, to processes for preparing the benzoquinolizines and to pharmaceutical preparations containing them.

U.K. Patent Specification No. 1,513,824 discloses that benqoquinolizines of the general formula (I)

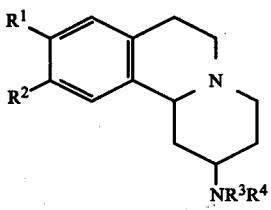

and the pharmaceutically acceptable acid addition salts thereof, wherein $R^1$ and $R^2$ which may be the same or different, each represent hydrogen, lower alkyl, lower alkoxy or halogen, $R^3$ represents hydrogen, lower alkyl or aryl and $R^4$ represents $-SO_2R^5$ (where $R^5$ is lower alkyl or aryl), $-CONH_2$ or $-CXNHR^6$ (where X is oxygen or sulphur and $R^6$ is aryl or aryl.CO.-), generally exhibit hypotensive activity upon administration to warm-blooded animals.

We have now found that a small group of compounds falling within general formula (I) but not specifically disclosed in the above mentioned specification, and their pharmaceutically acceptable acid addition salts possess high $\alpha_2$(presynaptic $\alpha$)-adrenoceptor antagonistic activity in warm blooded animals. This activity is not disclosed or foreshadowed in the above mentioned specification.

Accordingly the present invention provides benzoquinolizines of the general formula (II)

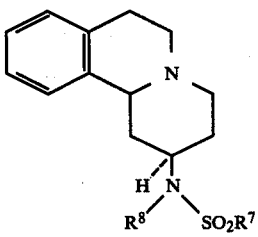

and the pharmaceutically acceptable acid addition salts thereof, wherein $R^7$ is lower alkyl or a phenyl or naphthyl radical optionally substituted by one or more lower alkyl, lower alkoxy or halogen substituents and $R^8$ is methyl or ethyl.

The term "lower" as used herein means that the radical referred to contains 1 to 6 carbon atoms. Preferably the radical contains 1 to 4 carbon atoms. For example a lower alkyl may be methyl, ethyl, propyl or butyl and a lower alkoxy group may be methoxy, ethoxy, propoxy or butoxy. Examples of halogen substituents include fluorine, chlorine and bromine. When $R^7$ is lower alkyl it is preferably methyl, propyl or isobutyl. Preferably $R^8$ is methyl.

Preferred compounds of formula (II) are

N-methyl-N-(1,3,4,6,7,11bα-hexahydro-2H-benzo[a]-quinolizin-2β-yl)methanesulphonamide
N-methyl-N-(1,3,4,6,7,11bα-hexahydro-2H-benzo[a]-quinolizin-2β-yl)propan-1-sulphonamide
N-methyl-N-(1,3,4,6,7,11bα-hexahydro-2H-benzo[a]-quinolizin-2β-yl)benzenesulphonamide
N-methyl-N-(1,3,4,6,7,11bα-hexahydro-2H-benzo[a]-quinolizin-2β-yl)-iso-butanesulphonamide and their pharmaceutically acceptable acid addition salts.

The compounds of the invention were tested for their $\alpha_2$-adrenoceptor antagonistic activity on the rat field stimulated vas deferens preparation using a modification of the method of Drew, Eur.J.Pharmac., 1977, 42, 123-130. The procedure is described below.

Desheathed vasa deferentia from sexually mature rats were suspended in a 6 ml organ bath in Krebs solution at 37° and bubbled with 5% $CO_2$ in oxygen. Platinum ring electrodes were positioned above and below the tissue for field stimulation, the stimulus parameters being 0.1 Hz 1 ms pulse width at supramaximal voltage. Twitch responses were recorded isotonically with a 0.5 g loading. Clonidine hydrochloride was used as the $\alpha$-adrenoceptor agonist and cumulative concentration-response curves were constructed for the inhibition of twitch obtained with clonidine in the range 0.125 to 4 ng ml$^{-1}$. After washing out clonidine, the twitch response quickly recovered and an antagonist was then introduced into the Krebs reservoir. Clonidine concentration-response curves were repeated 90 min after introduction of the antagonist. The concentration of clonidine producing 50% inhibition of twitch before and after introduction of antagonist were obtained and the dose-ratio for clonidine was calculated. Various concentrations of the antagonists were used.

These results were plotted in the manner described by Arunlakshana & Schild, Br.J.Pharmac. Chemother., 1959, 14, 48-58 and the values of $pA_2$ and slope were calculated. The compounds of the invention possess potent $\alpha_2$(presynaptic $\alpha$)-adrenoceptor antagonistic activity having, in general, values of $pA_2$ of 7.5 or more and substantially greater than other compounds of general formula I as is shown in the following Table I:

TABLE I

| Compound | $pA_2$ ($\alpha_2$) |
|---|---|
| Compounds of the invention | |
| A. N—methyl-N—(1,3,4,6,7,11bα-hexahydro-2H—benzo[a]quinolizin-2β-yl)methane-sulphonamide | 7.7 |
| B. N—methyl-N—(1,3,4,6,7,11bα-hexahydro-2H—benzo[a]quinolizin-2β-yl)ethane-sulphonamide | 7.7 |
| C. N—methyl-N—(1,3,4,6,7,11bα-hexahydro-2H—benzo[a]quinolizin-2β-yl)propan-1-sulphonamide | 8.3 |
| D. N—methyl-N—(1,3,4,6,7,11bα-hexahydro-2H—benzo[a]quinolizin-2β-yl)methane-sulphonamide | 8.4 |
| E. N—Ethyl-N—(1,3,4,6,7,11bα-hexahydro-2H—benzo[a]quinolizin-2-62 -yl)methane-sulphonamide | 7.8 |
| F. N—methyl-N—(1,3,4,6,7,11bα-hexahydro-2H—benzo[a]quinolizin-2β-yl)toluene-4-sulphonamide | 8.1 |
| G. N—methyl-N—(1,3,4,6,7,11bα-hexahydro-2H—benzo[a]quinolizin-2β-yl)-4-methoxy-benzenesulphonamide | 8.1 |
| H. N—methyl-N—(1,3,4,6,7,11bα-hexahydro-2H—benzo[a]quinolizin-2β-yl)-4-chloro-benzenesulphonamide | 7.6 |
| I. N—methyl-N—(1,3,4,6,7,11bα-hexahydro-2H-benzo[a]quinolizin-2β-yl)-2-methyl-benzenesulphonamide | 7.9 |

TABLE I-continued

| Compound | pA$_2$ ($\alpha_2$) |
|---|---|
| J. N—methyl-N—(1,3,4,6,7,11bα-hexahydro-2H—benzo[a]quinolizin-2β-yl)-3,4-dichlorobenzenesulphonamide | 7.5 |
| K. N—methyl-N—(1,3,4,6,7,11bα-hexahydro-2H-benzo[a]quinolizin-2β-yl)-n-butane-sulphonamide | 7.9 |
| L. N—methyl-N—(1,3,4,6,7,11bα-hexahydro-2H—benzo[a]quinolizin-2β-yl-iso-butane-sulphonamide | 8.5 |
| *Other compounds of formula I* | |
| 2-methanesulphonamido-1,3,4,6,7,11b-hexahydro-2H—benzo[a]quinolizine | 6.9 |
| N—methyl-N—(9,10-dimethoxy-1,3,4,6,7,11bα-hexahydro-2H—benzo[a]quinolizin-2β-yl)-methanesulphonamide | 6.8 / 6.8 |
| N—(n-Propyl)-N—(1,3,4,6,7,11bα-hexahydro-2H—benzo[a]quinolizin-2β-yl)methanesulphonamide | 7.0 |
| 2β-(n-propanesulphonamido-1,3,4,6,7,11bα-hexahydro-2H—benzo[a]quinolizine | 6.5 |
| 1-(1,3,4,6,7,11b-hexahydro-2H benzo[a]quinolizin-2yl)-3-phenyl urea | 5.4 |
| 1-(1,3,4,6,7,11b-hexahydro-2H—benzo[a]quinolizin-2yl)-3-phenylthiourea | 5.6 |
| 2β-phenylsulphonamido-1,3,4,6,7,11b-hexahydro-2H—benzo[a]quinolizine | 6.4 |
| 2βethanesulphonamido-1,3,4,6,7,11b-hexahydro-2H—benzo[a]quinolizine | 5.3 |

The compounds of the invention have been found to antagonize the presynaptic α-adrenoceptors to a much greater extent than the postsynaptic α-adrenoceptors. The postsynaptic($\alpha_1$)antagonistic activity can be evaluated by a number of different methods. One method involves assessing the activity on the isolated anococcygeus muscle of the rat. The method is based on that of Gillespie, Br.J.Pharmac., 1972, 45, 404–416. In the procedure male rats (250–360 g) are killed by a blow on the head and bled. The two anococcygeus muscles are removed from their position in the midline of the pelvic cavity, where they arise from the upper coccygeal vertebrae. The muscles are suspended in 5 ml organ baths in Krebs solution containing $10^{-4}$ M ascorbic acid, to prevent drug oxidation. The tissues are gassed with a 95% oxygen, 5% CO$_2$ mixture and maintained at 37°. Longitudinal muscle contractions are recorded using isotonic transducers. Cumulative dose response curves are then obtained to phenylephrine or in some cases methoxamine, both agents being postsynaptic alpha adrenoceptor agonists. The concentration range of phenylephrine or methoxamine used is 0.02 to 0.8 μg.ml$^{-1}$. The agonist is then washed from the bath and the test drug added to the bathing medium at a concentration of $10^{-6}$ M. After 30 min. equilibration with the test drug a further agonist dose response curve is obtained. The washing, equilibration and agonists dosing procedures are then repeated using $10^{-5}$ M and $10^{-4}$ M solutions of the test drug. Estimates of the pA$_2$ value for the test drug as an antagonist of phenylephrine or methoxamine were made from the agonist dose-ratios using the method of Arunlakshana & Schild, Br.J.Pharmac.Chemother., 1959, 14, 48–58.

The pA$_2$ for postsynaptic ($\alpha_1$) antagonistic activity and the $\alpha_2$ (presynaptic) selectivity (pA$_2$ presynaptic antagonistic activity/pA$_2$ postsynaptic antagonistic activity) for the compounds of the invention are given in Table II below. In this table the compounds are referred to by the references given in Table I.

TABLE II

| Compound | pA$_2$ (postsynaptic) | $\alpha_2$ selectivity |
|---|---|---|
| A | 5.95 | 56 |
| B | 6.17 | 34 |
| C | 6.14 | 144 |
| D | 6.34 | 102 |
| E | 6.25 | 35.5 |
| F | 6.33 | 59 |
| G | 6.5 | 40 |
| H | 6.09 | 32 |
| I | 6.27 | 40 |
| J | 5.48 | 93 |
| K | 6.6 | 19 |
| L | 6.49 | 93 |

The compounds of the invention possess $\alpha_2$ adrenoceptor antagonist activity and have a high $\alpha_2$ antagonist selectivity and hence are of value in conditions where selective antagonism of the $\alpha_2$-adrenoceptor is desirable, for example as antidepressants, in treatment of diabetes and in inhibiting blood platelet aggregation. For example it has been shown that representative compounds of the invention, e.g. N-methyl-N-(1,3,4,6,7,11bα-hexahydro-2H-benzo[a]quinolizin-2β-yl)methanesulphonamide, N-methyl-N-(1,3,4,6,7,11bα-hexahydro-2H-benzo[a]quinolizin-2β-yl)benzenesulphonamide and N-methyl-N-(1,3,4,6,7,11bα-hexahydro-2H-benzo[a]quinolizin-2β-yl)-iso-butanesulphonamide when administered to rats at 10 mg/kg inhibited the hyperglycaemia induced by the subcutaneous injection of 15 μg/kg of the $\alpha_2$ agonist clonidine. Also representative compounds of the invention, e.g. N-methyl-N-(1,3,4,6,7,11bα-hexahydro-2H-benzo[a]quinolizin-2β-yl)-methanesulphonamide and N-methyl-N-(1,3,4,6,7,11bα-hexahydro-2H-benzo[a]quinolizin-2β-yl)propan-1-sulphonamide have been shown to inhibit the aggregation in vitro of human blood platelets induced by adrenaline. Some of the compounds of the invention, particularly compound A above, do not possess substantial hypotensive activity when tested by a standard pharmacological procedure employing rats rendered hypertensive by implantation of desoxycorticosterone acetate.

The compounds of the present invention can be prepared by reacting a reactive derivative of a sulphonic acid derivative of general formula (III)

R$^7$SO$_2$OH      (III)

where R$^7$ has the meaning given above with 2β-ethylamino or methylamino-1,3,4,6,7,11b-hexahydro-2H-benzo[a]quinolizine and, if required, converting a free base into a pharmaceutically acceptable acid addition salt. The reactive derivative of the sulphonic acid can be, for example, the acid halide or anhydride. Preferably it is the halide i.e. a compound of general formula R$^7$SO$_2$X (where R$^7$ is as defined above and X is halogen, preferably chlorine). The reaction is preferably carried out under basic conditions, for example in the presence of a tertiary amine, e.g. triethylamine.

If in the process described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compound.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The 2β-ethylamino or methylamino-1,3,4,6,7,11b-hexahydro-2H-benzo[a]quinolizine starting materials for the above process can be prepared from the corresponding 2-oxo-compound by the procedure described in U.K. Patent Specification No. 1,513,824. Alternatively the 2-methylamino starting material can be prepared from the corresponding 2-amino compound, e.g. by reacting the amino compound with an alkylhaloformate or with formic acid and reducing, e.g. with a hydride transfer reagent such as lithium aluminium hydride the resulting 2—NHCO$_2$Alkyl or 2—NHCHO intermediate.

The invention further provides a pharmaceutical composition comprising a compound of general formula (II) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilised by, for example, intramuscular, intaperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in a unit dose of composition may be varied or adjusted from 0.5 mg or less to 750 mg or more, according to the particular need and the activity of the active ingredient. The invention also includes the compounds in the absence of the carrier where the compounds are in unit dosage form.

The following Examples illustrate the invention:

EXAMPLE 1

2β-Methylamino-1,3,4,6,7,11bα-hexahydro-2H-benzo[a]quinolizine (a) 2β-Amino-1,3,4,6,7,11bα-hexahydro-2H-benzo[a]quinolizine (17.7 g) was cooled to 0° (ice) and cautiously treated with 100% formic acid (100 cm$^3$). The mixture was stirred until homogenous, then slowly treated with acetic anhydride (10.0 g) over above 1 hour at 0°. After stirring for a further 1 hour, the mixture was heated to reflux for 2 hours, cooled and excess solvent evaporated in vacuo. The residual oil was basified with 10% aq. Na$_2$CO$_3$ (ca. 500 cm$^3$) and extracted with dichloromethane (3×100 cm$^3$). The combined extracts were washed with brine (100 cm$^3$) and dried (MgSO$_4$). Glc at this stage revealed incomplete reaction (ca. 50%), and the entire cycle was repeated with fresh formic acid and acetic anhydride. Evaporation of the organic extract gave a mixture of solid and oil (16.4 g). Crystallisation from ethanol-60/80 petrol afforded pure N-[1,3,4,6,7,11bα-hexahydro-2H-benzo-(a)-quinolizin-2β-yl]formamide (7.12 g) as off-white micro-needles, mp 162°–4° (partial decomposition occurs above 147°).

(b) A suspension of the product of part (a) (7.3 g) in dry THF (80 cm$^3$) was added slowly to a solution of lithium aluminium hydride (4 g) in dry THF (120 cm$^3$). The mixture was stirred and heated to reflux for 24 hours under a blanket of dry nitrogen, then decomposed by the dropwise addition of water (4 cm$^3$), 15% aq. NaOH (4 cm$^3$) and water (12 cm$^3$). After filtration, the solution was evaporated, the residue taken up in dichloromethane, dried (MgSO$_4$), filtered and evaporated to give a red-brown oil (6.19 g) virtually pure by tlc, which set solid on standing.

A sample (0.57 g) was converted to the hydrochloride in ethanol (7 cm$^3$) and ethanolic hydrogen chloride. On cooling, crystals were obtained which were filtered off, washed with 1:2 ethanol/ethyl acetate and dried in vacuo to give pure 2β-methylamino-1,3,4,6,7,11bα-hexahydro-2H-benzo[a]quinolizine hydrochloride (0.67 g; 88.2%) as colourless micro-needles, mp 248°-251° (dec.) (fast rate of heating; decomposition begins at temperatures above 200°).

EXAMPLE 2

N-Methyl-N-(1,3,4,6,7,11bα-hexahydro-2H-benzo[a]quinolizin-2β-yl)methanesulphonamide 2β-Methylamino-1,3,4,6,7,11bα-hexahydro-2H-benzo[a]quinolizine (1.88 g) and triethylamine (0.90 g) were dissolved in ice-cold dichloromethane (10 cm$^3$) and treated with an ice-cold solution of methane sulphonyl chloride (1.00 g) in dichloromethane (5 cm$^3$). The clear solution was allowed to stand overnight. The resulting mixture of crystals and solution was diluted with dichloromethane (10 cm$^3$) and water (5 cm$^3$), and extracted with water (2×20 cm$^3$). The organic layer was separated and dried (MgSO$_4$). Filtration and evaporation gave a pink gum (2.37 g). The hydrochloride was prepared from ethanolic hydrogen chloride, and recrystallised from ethanol-ethyl acetate, to yield the title compound hydrochloride as off-white micro-needles (1.45 g), mp 198°-200° (dec).

EXAMPLE 3

N-Methyl-N-(1,3,4,6,7,11bα-hexahydro-2H-benzo[a]quinolizin-2β-yl)ethanesulphonamide A solution of ethanesulphonyl chloride (1.45 g) in dichloromethane (20 cm$^3$) was added slowly to an ice-cold solution of 2β-methylamino-1,3,4,6,7,11bα-hexahydro-2H-benzo[a]quinolizine and triethylamine (1.2 g; 0.0119 M) in dichloromethane (30 cm$^3$). The clear mixture was stirred briefly, then kept at room temperature for 7 days, when tlc showed that the reaction was complete. It was washed with water (2×25 cm$^3$) and dried (MgSO$_4$). Filtration and evaporation afforded a yellow-orange syrup (3.13 g) which was dissolved in hot ethanol (5 cm$^3$), acidified with ethanolic hydrogen chloride, diluted with ethyl acetate (15 cm$^3$) and cooled. The precipitated, sticky crystals were filtered off and washed with 1:3 ethanol/ethyl acetate. Two recrystallisations from 1:1 ethanol/ethyl acetate afforded the title compound as the hydrochloride (0.97 g), colourless crystals, mp 207°-212° (dec) (decomposition causes local melting above 180°).

EXAMPLE 4

N-Methyl-N-(1,3,4,6,7,11bα-hexahydro-2H-benzo[a]quinolizin-2β-yl)propan-1-sulphonamide An ice-cold, stirred solution of 2β-methylamino-1,3,4,6,7,11bα-hexahydro-2H-benzo[a]quinolizine (2.16 g) and triethylamine (1.1 g) in dichloromethane (25 cm$^3$) was slowly treated with a solution of n-propanesulphonyl chloride (1.43 g) in dichloromethane (25 cm$^3$). The clear solution was then kept at room temperature for 72 h, when tlc showed complete reaction had occurred. The mixture was washed with water (2×25 cm$^3$), dried (MgSO$_4$), filtered and evaporated to give a viscous, pale-yellow oil (3.09 g). This was dissolved in hot ethanol (7 cm$^3$), acidified with ethanolic hydrogen chloride, diluted with ethyl acetate (25 cm$^3$) and cooled, with scratching. The crystals which slowly separated were collected by filtration, washed with 20% ethanol-ethyl acetate and recrystallised from methanol to give the title compound as the hydrochloride (1.98 g), colourless plates, m.p. approx. 222°-240° (dec. violent decomposition occurring about 200° without melting).

EXAMPLE 5

N-Methyl-N-(1,2,4,6,7,11bα-hexahydro-2H-benzo[a]quinolizin-2β-yl)benzenesulphonamide An ice-cold, stirred solution of 2β-methylamino-1,3,4,6,7,11bα-hexahydro-2H-benzo[a]quinolizine and triethylamine (0.7 g) in dichloromethane (25 cm$^3$) was slowly treated with a solution of benzenesulphonyl chloride (1.2 g) in dichloromethane (25 cm$^3$). The clear solution was kept at room temperature for 72 h when tlc showed complete reaction had occurred. The mixture was washed with water (2×25 cm$^3$), dried (MgSO$_4$), filtered and evaporated to give an off-white glass (2.44 g). This was dissolved in ethanol (7 cm$^3$), acidified with ethanolic HCl, diluted with ethyl acetate (10 cm$^3$) and cooled. The crystals were filtered off and washed with 1:1 ethanol/ethyl acetate to give the title compound as the hydrochloride (2.32 g), colourless needles, m.p. 225°-228° (dec, partial decomposition occurring above 193°).

EXAMPLE 6

N-Ethyl-N-(1,2,3,4,6,7,11bα-hexahydro-2H-benzo[a]quinolizin-2β-yl)methanesulphonamide An ice-cold solution of 2-ethylamino-1,3,4,6,7,11b-hexahydro-2H-benzo[a]quinolizine (1.35 g) and triethylamine (0.60 g) in dichloromethane (50 cm$^3$) was treated, with stirring, with a solution of dimesyl anhydride (1.02 g) in dichloromethane (25 cm$^3$). The mixture was stirred for a further 2 h, then allowed to stand at room temperature until tlc indicated that reaction was virtually complete (11 days). The mixture was then washed with water (2×25 cm$^3$), dried (MgSO$_4$), filtered and evaporated to give an oil (1.59 g). Chromatography on silica eluted with 5-10% ethanol/ethyl acetate afforded a purified product (0.88 g) which was acidified with ethanolic hydrogen chloride and, after evaporation of the solvent, crystallised from iso-propanol. The crystals were recrystallised from boiling ethanol (3 cm$^3$) to which ethyl acetate (5 cm$^3$) was added, to give pure title compound as the hydrochloride quaterhydrate (0.55 g), colourless crystals, m.p. 217°-223° (dec) (with sublimation and partial decomposition above 200°).

EXAMPLE 7

N-Methyl-N-(1,3,4,6,7,11bα-hexahydro-2H-benzo[a]quinolizin-2β-yl)toluene-4-sulphonamide A stirred solution of 2β-methylamino-1,3,4,6,7,11bα-hexahydro-2H-benzo[a]quinolizine (2.16 g) and triethylamine (1.1 g) in dichloromethane (25 cm$^3$) was cooled in ice and treated with a solution of tosyl chloride (1.91 g) in dichloromethane (25 cm$^3$). The clear mixture was kept at room temperature for 6 days, then washed with water (2×25 cm$^3$) and dried (MgSO$_4$). Filtration and evaporation afforded a red-orange glass (3.69 g) which crystallised from hot ethanol (10 cm$^3$). After cooling, the crystals were filtered off and washed with ice-cold ethanol to give the title compound (4.43 g) as cream crystals, m.p. 161°-164°.

Trituration with boiling ethanol and acidification with ethanolic HCl (which caused dissolution followed by re-precipitation), followed by stirring to break up lumps and filtration afforded the pure hydrochloride (3.39 g) as light buff rods, m.p. 258°–261° (dec; decomposition occurred at all temperatures above 220°).

EXAMPLE 8

N-Methyl-N-(1,3,4,6,7,11bα-hexahydro-2H-benzo[a]-quinolizin-2β-yl)-4-methoxybenzenesulphonamide An ice-cold, stirred solution of 2β-methylamino-1,3,4,6,7,11bα-hexahydro-2H-benzo[a]quinolizine (2.16 g) and triethylamine (1.1 g) in dichloromethane (25 cm³) was treated with a solution of p-methoxybenzenesulphonyl chloride (2.07 g) in dichloromethane (25 cm³). After standing for 7 days, the solution was washed with water (2×25 cm³), dried (MgSO₄) and evaporated to give a residue (3.61 g) which was crystallised from ethanol (15 cm³) to give the title compound as cream crystals, m.p. 154°–6°.

The base was triturated with boiling ethanol (10 cm³), acidified with ethanolic HCl (which caused partial dissolution followed by reprecipitation), cooled and stirred well to break up lumps. Filtration gave off-white crystals which were triturated well with a boiling mixture of ethanol/methanol/water. After cooling, the crystals were filtered off and washed well with ethanol, to give the title compound as the hydrochloride (2.62 g) as pale buff crystals with no clear m.p. (decomp. occurs above 220°).

EXAMPLE 9

N-Methyl-N-(1,3,4,6,7,11bα-hexahydro-2H-benzo[a]-quinolizin-2β-yl)-4-chlorobenzenesulphonamide An ice-cold, stirred solution of 2β-methylamino-1,3,4,6,7,11bα-hexahydro-2H-benzo[a]quinolizine (1.08 g) and triethylamine (0.55 g) in dichloromethane (25 cm³) was treated with a solution of 4-chlorobenzenesulphonyl chloride (1.06 g) in dichloromethane. The mixture was kept at room temperature for 7 days, then washed with water (2×25 cm³), dried (MgSO₄), filtered and evaporated to give the title compound as a brown semi-crystalline gum (1.64 g) which crystallised from hot ethanol (5 cm³) to give pale-buff crystals, m.p. 50°–3° (dec).

The crystals were taken up in boiling ethanol (10 cm³), acidified with ethanolic HCl (causes partial dissolution followed by re-precipitation), cooled and stirred well. Filtration gave very pale pink crystals which were triturated with a hot ethanol/methanol/water mixture, cooled, filtered and washed with ethanol to give the title compound hydrochloride (1.10 g), colourless, short plates, with no clear m.p. (decomp. occurs above 230°).

EXAMPLE 10

N-Methyl-N-(1,3,4,6,7,11bα-hexahydro-2H-benzo[a]-quinolizin-2β-yl)-2-methylbenzenesulphonamide An ice-cold, stirred solution of 2β-methylamino-1,3,4,6,7,11bα-hexahydro-2H-benzo[a]quinolizine (1.84 g) and triethylamine (0.9 g) in dichloromethane (25 cm³) was slowly treated with a solution of o-toluenesulphonyl chloride (1.62 g) in dichloromethane (25 cm³). The solution was kept at room temperature for 2 days, then washed with water (2×50 cm³) and dried (MgSO₄). Filtration and evaporation afforded an orange syrup (3.37 g) which was dissolved in hot ethanol (10 cm³), acidified with ethanolic HCl and cooled. The crystals were filtered off after 1 hour, and washed with ethanol to give the title compound as the hydrochloride (2.88 g) as pale cream crystals. Recrystallisation from ethanol/water gave the pure hydrochloride, quaterhydrate (2.03 g) as colourless needles, m.p. 197°–203° (dec; decomp. occurred above 175°).

EXAMPLE 11

N-Methyl-N-(1,3,4,6,7,11bα-hexahydro-2H-benzo[a]-quinolizin-2β-yl)-3,4-dichlorobenzenesulphonamide An ice-cold, stirred solution of 2β-methylamino-1,3,4,6,7,11bα-hexahydro-2H-benzo[a]quinolizine (1.84 g) and triethylamine (0.9 g) in dichloromethane (25 cm³) was slowly treated with a solution of 3,4-dichlorobenzenesulphonyl chloride (2.09 g) in dichloromethane (25 cm³). The mixture was kept at room temperature for 2 days, then washed with water (2×50 cm³) and dried (MgSO₄). Filtration and evaporation afforded an off-white solid (3.30 g) which was purified by trituration with hot ethanol, to give pure title compound, m.p. 191°–3°.

A suspension of the sulphonamide in boiling ethanol (10 cm³) was acidified with ethanolic HCl and the clear solution cooled. Filtration and washing with ethanol gave the hydrochloride (3.03 g) as pale cream crystals. Recrystallisation from ethanol/water afforded the title compound as the pure hydrochloride, quarterhydrate (2.71 g), as colourless crystals, m.p. 195°–197° (dec).

EXAMPLE 12

N-Methyl-N-(1,3,4,6,7,11bα-hexahydro-2H-benzo[a]-quinolizin-2β-yl)-n-butanesulphonamide An ice-cold, stirred solution of 2β-methylamino-1,3,4,6,7,11bα-hexahydro-2H-benzo[a]quinolizine (2.16 g) and triethylamine (1.2 g) in dichloromethane (25 cm³) was treated with a solution of n-butanesulphonyl chloride (1.57 g) in dichloromethane (25 cm³). The clear solution was kept at room temperature for 4 days, washed with water (2×50 cm³) and dried (MgSO₄). Filtration and evaporation afforded a dark gum (2.96 g) which was chromatographed on silica eluted with 10% ethanol-ethyl acetate to give a pale yellow syrup (2.04 g). This was dissolved in hot ethanol (5 cm³), acidified with ethanolic HCl, diluted with ethyl acetate (20 cm³) and cooled. After several hours, the precipitated crystals were filtered, washed with ethyl acetate and dried at 60°/100 mm to give the title compound as the hydrochloride (2.25 g), colourless microplates, m.p. 224°–226° (dec.).

EXAMPLE 13

N-Methyl-N-(1,3,4,6,7,11bα-hexahydro-2H-benzo[a]-quinolizin-2β-yl)-isobutanesulphonamide (a) iso-Butanesulphonic acid, sodium salt, was prepared by hydrogenation of commercially available 2-methyl-2-propene-1-sulphonic acid, sodium salt, and converted to the sulphonyl chloride with POCl₃.

(b) An ice-cold, stirred solution of 2β-methylamino-1,3,4,6,7,11bα-hexahydro-2H-benzo[a]quinolizine (2.16 g; 0.01 M) and triethylamine (1.2 g; 0.012 M) in dichloromethane (25 cm³) was slowly treated with a solution of iso-butanesulphonyl chloride (1.57 g; 0.01 M) in dichloromethane (25 cm³). The clear solution was kept at room temperature for 6 days, washed with water (2×50 cm³) and brine, dried (MgSO₄), filtered and evaporated to give a brown syrup (3.22 g). Chromatography on silica eluted with 10% ethanol-ethyl acetate gave a yellow oil (2.75 g) which was dissolved in hot ethanol (5 cm³), acidified with ethanolic HCl, diluted with ethyl acetate (20 cm³) and cooled. After about ½ hour, the crystals were filtered off, washed with 10% ethanol-/ethyl acetate and dried at 80°/100 mm to give pure title compound (2.40 g) as colourless crystals, m.p. 210°-212° (dec.).

We claim:

1. A compound selected from the group consisting of a benzoquinolizine of the formula

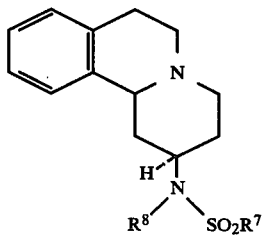

and a pharmaceutically acceptable acid addition salt thereof, wherein $R^7$ is lower alkyl or a phenyl or naphthyl radical optionally substituted by one or more lower alkyl, lower alkoxy or halogen substituents and $R^8$ is methyl or ethyl.

2. A compound according to claim 1 which is N-methyl-N-(1,3,4,6,7,11bα-hexahydro-2H-benzo[a]quinolizin-2β-yl)methanesulphonamide or a pharmaceutically acceptable acid addition salt thereof.

3. A compound according to claim 1 which is N-methyl-N-(1,3,4,6,7,11bα-hexahydro-2H-benzo[a]quinolizin-2β-yl)propan-1-sulphonamide or a pharmaceutically acceptable acid addition salt thereof.

4. A compound according to claim 1 which is N-methyl-N-(1,3,4,6,7,11bα-hexahydro-2H-benzo[a]quinolizin-2β-yl)benzenesulphonamide or a pharmaceutically acceptable acid addition salt thereof.

5. A compound according to claim 1 which is N-methyl-N-(1,3,4,6,7,11bα-hexahydro-2H-benzo[a]quinolizin-2β-yl)ethanesulphonamide or a pharmaceutically acceptable acid addition salt thereof.

6. A compound according to claim 1 which is N-ethyl-N-(1,3,4,7,11bα-hexahydro-2H-benzo[a]quinolizin-2β-yl)methanesulphonamide or a pharmaceutically acceptable acid addition salt thereof.

7. A compound according to claim 1 which is N-methyl-N-(1,3,4,6,7,11bα-hexahydro-2H-benzo[a]quinolizin-2β-yl)toluene-4-sulphonamide or a pharmaceutically acceptable acid addition salt thereof.

8. A compound according to claim 1 which is N-methyl-N-(1,3,4,6,7,11bα-hexahydro-2H-benzo[a]quinolizin-2β-yl)-4-methoxybenzenesulphonamide or a pharmaceutically acceptable acid addition salt thereof.

9. A compound according to claim 1 which is N-methyl-N-(1,3,4,6,7,11bα-hexahydro-2H-benzo[a]quinolizin-2β-yl)-4-chlorobenzenesulphonamide or a pharmaceutically acceptable acid addition salt thereof.

10. A compound according to claim 1 which is N-methyl-N-(1,3,4,6,7,11bα-hexahydro-2H-benzo[a]quinolizin-2β-yl)-2-methylbenzenesulphonamide or a pharmaceutically acceptable acid addition salt thereof.

11. A compound according to claim 1 which is N-methyl-N-(1,3,4,6,7,11bα-hexahydro-2H-benzo[a]quinolizin-2β-yl)-3,4-dichlorobenzenesulphonamide or a pharmaceutically acceptable acid addition salt thereof.

12. A compound according to claim 1 which is N-methyl-N-(1,3,4,6,7,11bα-hexahydro-2H-benzo[a]quinolizin-2β-yl)-n-butanesulphonamide or a pharmaceutically acceptable acid addition salt thereof.

13. A compound according to claim 1 which is N-methyl-N-(1,3,4,6,7,11bα-hexahydro-2H-benzo[a]quinolizin-2β-yl)-isobutanesulphonamide or a pharmaceutically acceptable acid addition salt thereof.

14. A pharmaceutical composition having $α_2$-adrenoceptor antagonistic activity comprising an amount effective to antagonise $α_2$ adrenoceptors of a compound selected from the group consisting of a benzoquinolizine of the formula

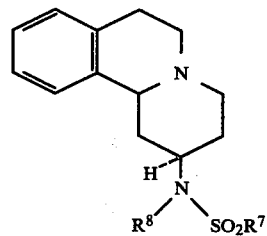

and a pharmaceutically acceptable acid addition salt thereof, wherein $R^7$ is lower alkyl or a phenyl or naphthyl radical optionally substituted by one or more lower alkyl, lower alkoxy or halogen substituents and $R^8$ is methyl or ethyl, in association with a pharmaceutically acceptable carrier.

15. A method of selectively antagonising $α_2$ adrenoceptors in warm blooded animals which comprises administering to the animal an effective amount of a compound selected from the group consisting of a benzoquinolizine of the formula

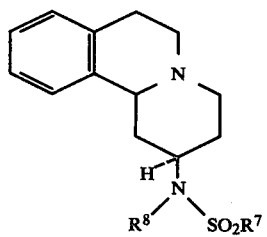

and a pharmaceutically acceptable acid addition salt thereof, wherein $R^7$ is lower alkyl or a phenyl or naphthyl radical optionally substituted by one or more lower alkyl, lower alkoxy or halogen substituents and $R^8$ is methyl or ethyl.

* * * * *